(12) United States Patent
VanTassel et al.

(10) Patent No.: US 6,645,143 B2
(45) Date of Patent: *Nov. 11, 2003

(54) PRESSURE/TEMPERATURE/FLOW MONITOR DEVICE FOR VASCULAR IMPLANTATION

(75) Inventors: Robert A. VanTassel, Excelsior, MN (US); Robert S. Schwartz, Rochester, MN (US); David R. Holmes, Rochester, MN (US)

(73) Assignee: Tricardia, L.L.C., Excelsior, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/961,564

(22) Filed: Sep. 20, 2001

(65) Prior Publication Data

US 2002/0072656 A1 Jun. 13, 2002

Related U.S. Application Data

(63) Continuation of application No. 09/416,661, filed on Oct. 12, 1999, now Pat. No. 6,309,350, which is a continuation-in-part of application No. 09/303,634, filed on May 3, 1999, now abandoned.

(51) Int. Cl.[7] .................................................. A61B 5/00
(52) U.S. Cl. ....................... 600/300; 600/486; 600/505; 600/500; 600/549
(58) Field of Search ................................ 600/300, 485, 600/486, 488, 500, 549, 504, 505

(56) References Cited

U.S. PATENT DOCUMENTS

| | | | |
|---|---|---|---|
| 3,874,388 A | 4/1975 | King et al. | |
| 4,836,204 A | 6/1989 | Landymore et al. | |
| 4,846,191 A | 7/1989 | Brockway et al. | |
| 4,917,089 A | 4/1990 | Sideris | |
| 5,334,217 A | 8/1994 | Das | |
| 5,411,551 A | 5/1995 | Winston et al. | 623/1 |
| 5,451,235 A | 9/1995 | Lock et al. | |
| 5,634,936 A | 6/1997 | Linden et al. | |
| 5,704,352 A | 1/1998 | Tremblay et al. | 128/630 |
| 5,725,552 A | 3/1998 | Kotula et al. | |
| 6,015,387 A * | 1/2000 | Schwartz et al. | 600/504 |
| 6,030,413 A * | 2/2000 | Lazarus | 623/1 |
| 6,053,873 A | 4/2000 | Govari et al. | 600/505 |
| 6,309,350 B1 * | 10/2001 | Van Tassel | 600/300 |

FOREIGN PATENT DOCUMENTS

| | | | |
|---|---|---|---|
| EP | 0 897 690 A1 | 2/1999 | A61B/5/00 |
| WO | WO 00/16686 | 3/2000 | A61B/5/00 |

* cited by examiner

*Primary Examiner*—Robert L. Nasser
(74) *Attorney, Agent, or Firm*—Bingham McCutchen LLP

(57) ABSTRACT

A medical monitoring apparatus designed to be implanted in the vascular system is capable of sensing and transmitting via a telemetry link to an external monitor both pressure and temperature information. An internally or externally powered microcircuit component is supported on a stent-like structure and adapted to be placed in the vascular system. Placement in the ventricular septum permits measurement of pressure and temperature in the left ventricle without introducing thrombus generating materials in the left ventricle.

27 Claims, 4 Drawing Sheets

PRESSURE/TEMPERATURE/FLOW MONITOR DEVICE FOR VASCULAR IMPLANTATION

CROSS-REFERENCE TO RELATED APPLICATION

This is a continuation of 09/416,661 filed on Oct. 12, 1999 now U.S. Pat. No. 6,309,350 which is a continuation-in-part of application Ser. No. 09/303,634, filed May 3, 1999 now abandoned.

BACKGROUND OF THE INVENTION

I. Field of the Invention

This invention relates generally to medical apparatus for monitoring physiologic parameters within the body of a human or other animal, and more particularly to an implantable device for chronic monitoring of pressure, flow and temperature within living humans or animals.

II. Discussion of the Prior Art

In the diagnosis and treatment of various maladies, a variety of devices have been developed which can be implanted within the body and used to monitor various physiologic parameters. With the advent of microminiature circuitry, it has become practical to implant a variety of sensors responsive to various physiologic changes, along with circuitry for the transcutaneous transmission of information from the implanted unit, via a telemetry link to an external recording/display device. For example, in the field of implantable cardiac pacemakers and defibrillators, sensing circuitry is incorporated therein for monitoring a number of physiologic parameters, such as respiratory rate, tidal volume, heart rate, blood temperature, movement, etc. Pacemaker leads have been developed that incorporate pressure transducers and temperature sensors such that the pacing rate of the implanted device can be made to vary in relation to detected changes in blood temperature and blood pressure.

In implementing such devices, the electronic circuitry is housed in a body compatible, fluid impervious housing along with a suitable power supply or AC to DC converter and electrical leads are then routed from the implant site and through the vascular system to a location on or in the heart. Because of concern that the presence of a lead in the left ventricular chamber may result in the formation of a thrombus that could break loose and reach the brain and cause stroke or embolize to another peripheral vessel, pacing leads or other devices are seldom inserted into the left ventricle, especially for chronic monitoring or therapy delivery.

The ability to measure left ventricular pressure or its surrogate in the ambulatory patient, non-invasively, has great potential in determining the status of heart failure patients, providing an opportunity to modify medical management of ventricular dysfunction very precisely as compared to current clinical practice. Moreover, ambulatory hypertensive patients can be managed more closely when peak systolic and diastolic pressure can be chronically monitored.

The ability to measure myocardial temperature with an implanted device and to thereafter telemeter the temperature information to an external monitor will permit cardiac transplant patients to be closely managed. It is believed that rejection in organ transplant patients manifest early as a small tissue temperature elevation due to the inflammatory reaction of rejection. The only presently available method to determine transplant status is to perform a biopsy, an invasive procedure that is sometimes done weekly or more often, and is done in such a patient hundreds of times during that patient's life. A device for measuring tissue temperature and telemetering the information to an external monitor would limit the number of times such biopsy is required—a significant clinical advance.

Myocardial temperature sensing is beneficial in the management of heart failure. Ventriculo-vascular coupling and impedance mismatches manifest themselves as excess heating of the ventricle. By having temperature monitoring available, accurate titration of preload and afterload reducing medication could be achieved to limit myocardial energy output and thereby the heart will perform more efficiently. Therefore, a need exists for a system for chronically monitoring temperature and pressure within the left ventricular and/or atrial chambers of the heart or myocardial tissue.

It has also determined that a temperature sensor located in the pulmonary artery branches for sensing lung tissue temperature can provide meaningful information following heart/lung transplant surgery in that an elevated blood or lung tissue temperature in the pulmonary artery or branches may be indicative of the onset of rejection, allowing interventional adjustment in the amount of anti-rejection drug being administered to, the patient. We are presently unaware of any temperature sensor that can be chronically implanted to measure temperature changes in blood traversing the pulmonary artery.

By locating the monitor implant at other locations within the body, renal, hepatic or pancreas transplant status can be assessed. Locating the device in the peripheral blood vessels can allow assessment of exercise capacity. The monitor may also be used to calculate blood flow using thermodilution techniques.

From the foregoing, it can be seen a need exists for an implantable sensor especially designed for placement in a selected portion of a patient's vascular system and which can be used to chronically transmit pressure and/or temperature data to an external monitor/display unit so that a medical professional can more readily diagnosis and treat various medical conditions. It is principal object of the present invention to fulfill this need.

SUMMARY OF THE INVENTION

In accordance with the present invention there is provided a medical monitoring apparatus that comprises a support member that is adapted for chronic implantation at a predetermined location within the vascular system of a living human or other animal. One or more sensor devices are affixed to the support means for sensing at least one measurable physiologic parameter. The apparatus further includes a means for telemetrically transmitting signals representative of the sensed parameter percutaneously to an external signal receiver. In accordance with one embodiment of the invention, the support means may comprise a self-expanding or balloon expandable tubular stent that is adapted for chronic implantation at a predetermined location in the vascular system and affixed to the tubular stent is an electronic circuit for measuring a physiologic parameter. The electronic circuit means also includes a means for telemetrically transmitting signals representative of the sensed parameter percutaneously to a signal receiver external to the body of the living animal.

To measure left ventricular pressure/temperature, the apparatus of the present invention may be placed in an puncture made through the ventricular septum with the stent being anchored in this opening, such that the pressure/ temperature sensor is exposed to blood or tissue in the left ventricle. An anchoring arrangement is provided on the stent to prevent the normal pumping action of the heart from displacing the implanted stent. To prevent blood flow through the tubular stent, the lumen thereof may be packed with a fibrous material for occluding the opening. The electronics module may also be located in the lumen if occlusion is desired.

If the stent device is to be placed in the pulmonary or some other artery of a patient, the anchoring means may comprise a series of hooks that become engaged with the inner wall of the artery when the stent is allowed to or made to expand radially during its implantation.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
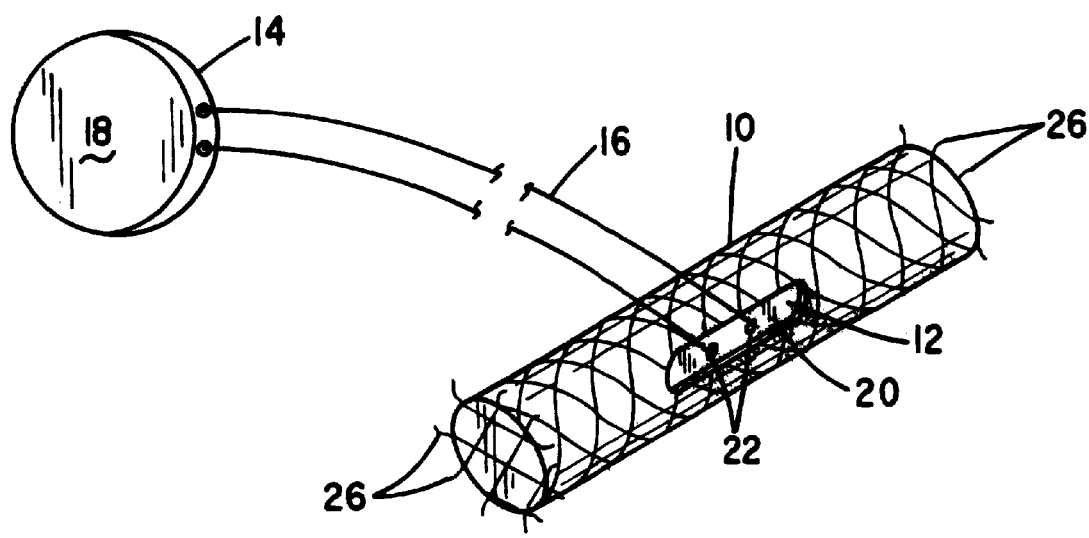
FIG. 1 is a perspective view showing a tubular stent as a support member for an electronic circuit package for sensing and telemetrically transmitting sensed pressure and temperature data and powered by an implantable power pack.

Referring first to FIG. 1, there is illustrated a first embodiment of a temperature/pressure monitoring device adapted for placement at a desired location within the vascular system of a living animal. It is seen to comprise a support member 10, here shown as a self-expandable or balloon expandable stent, to which is attached an electronics module 12 that is adapted to be powered by an implantable power source 14 connected to it by means of conductors 16. The power source 14 is preferably a lithium-iodide battery contained within a body fluid impervious housing 18. The electronic circuitry comprising the module 12 is also contained within a body fluid impervious housing 20 having sealed electrical feed-throughs 22 to which the conductors 16 are attached for bringing DC power into the module.

As will be further explained, associated with the electronics module 20 are one or more sensors for detecting changes in a physiologic parameter such as blood temperature, blood pressure or flow. The sensor may comprise a pressure sensor of the type described in the Brockway et al. U.S. Pat. No. 4,846,191, either alone or in combination with a thermistor temperature transducer and a Doppler flow sensor.

Figure 2:
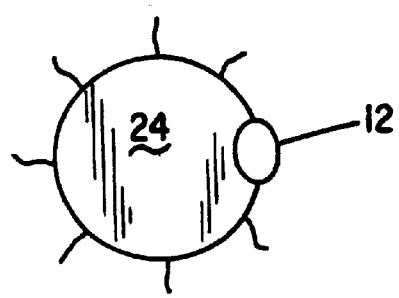
FIG. 2 is an end view of the device of FIG. 1.

Formed on opposed ends of the stent 10 are retention elements, shown in FIG. 2 as hooks 26 which are adapted to engage tissue to prevent migration of the device from its desired implant site. The need for retention elements is, of course, somewhat dependent on the location selected for the implant.

Figure 3:
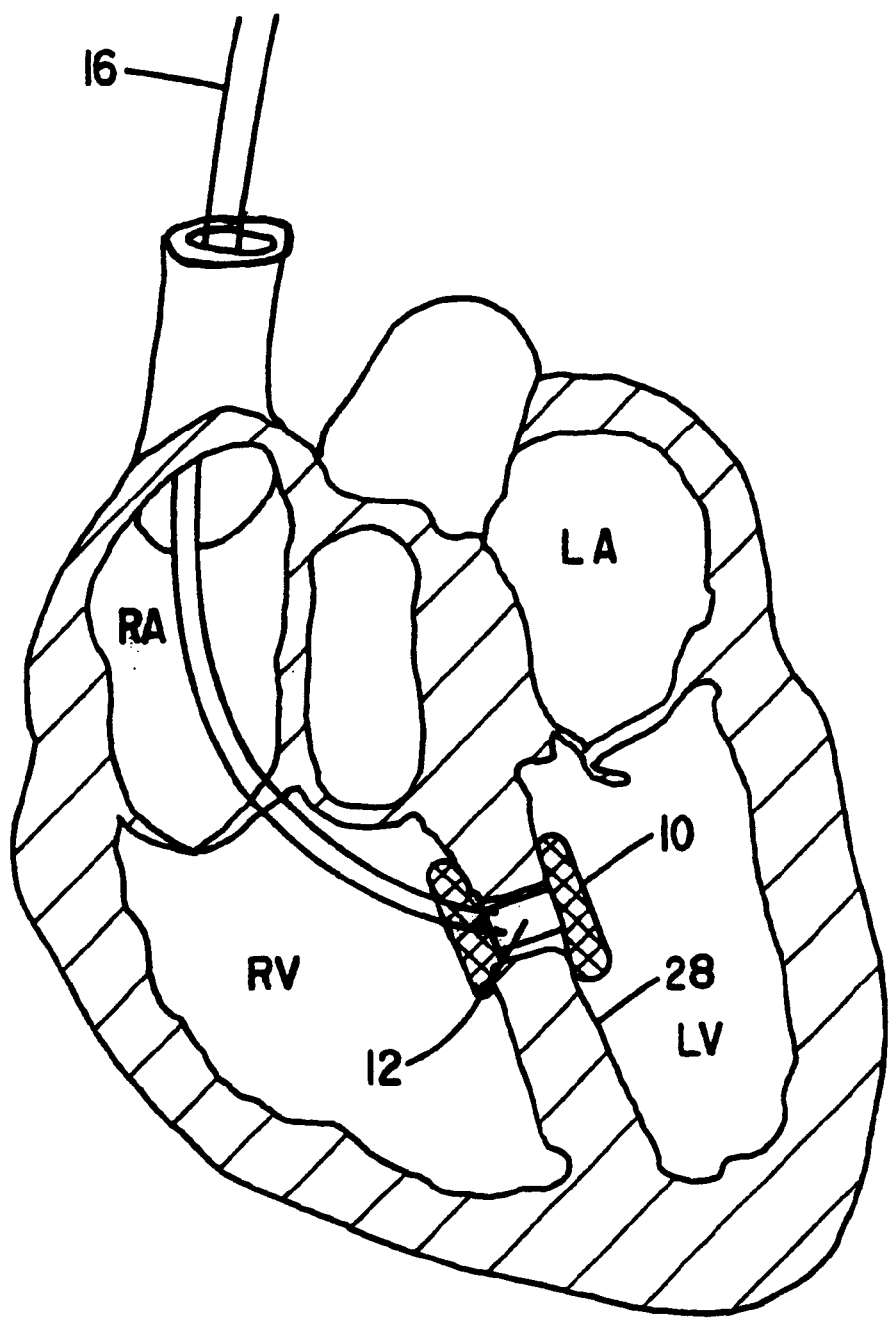
FIG. 3 is a sectioned view through the heart showing the monitor device of the present invention located in the ventricular and atrial septum.

The sectional view taken through a heart illustrated in FIG. 3 shows the way in which the present invention can be used to monitor either left ventricular pressure or left atrial pressure on a chronic basis. Here, an incision is made through the ventricular septum 28 or the atrial septum 30 with a device like that shown in FIG. 1 percutaneously implanted via an artery or vein and inserted into the surgically created opening. The support device 10, itself, may comprise a septal defect occluder fashioned after that described in the Kotula et al. U.S. Pat. No. 5,725,552 but with an electronics module 12 mounted thereon. The sensor element is exposed to the blood in the left ventricle and/or the left atrial chamber depending on the placement of the device. The support device 10 may be delivered by way of a catheter routed through the vascular system into the right ventricle and thence through the surgically created septal opening. When the device 10 is released from the confines of the catheter, it self-expands to a predetermined dumbbell configuration, as illustrated, to maintain it in position in the septal wall. Alternatively, in an open heart surgery, the device of FIG. 1 can be inserted through the myocardium of the left ventricle or left atrium.

When disposed in the lumen of a blood vessel, the support device 10 is tubular as shown in FIG. 1, permitting blood flow therethrough. The hooks 26 on opposed ends thereof serve to anchor the device in place in the selected blood vessel. Placement of the stent with its temperature/pressure/flow measuring circuitry in the pulmonary artery or a branch thereof can be used to obtain a good estimation of left ventricular end diastolic pressure which is meaningful in the treatment of CHF and hypertension. It is calibrated by direct comparison with left ventricular pressure measured with an acutely placed pressure sensing catheter. Periodic recalibration can be accomplished via software.

Figure 4:
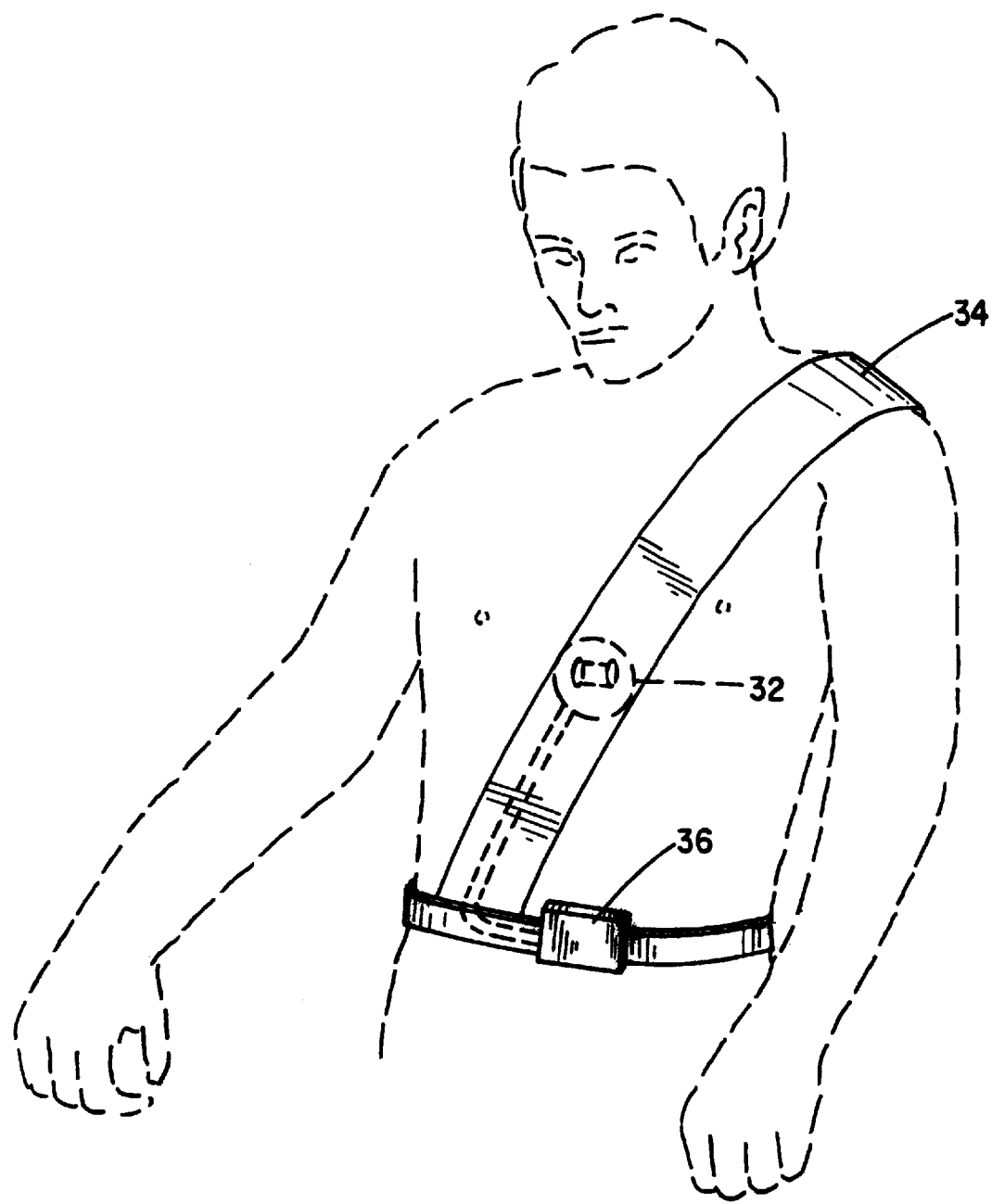
FIG. 4 is a schematic diagram illustrating apparatus for applying power to an implanted unit percutaneously.

FIG. 4 illustrates an alternative embodiment of the invention wherein the implant device may receive its operating power transcutaneously from a programmer transducing head 32 supported on a shoulder strap 34 which keeps the transducing head is oriented in alignment with the implanted device. The transducing head 32 may be of the type used in the telemetry link of a programmable implantable pacemaker allowing the patient to be ambulatory. The transmitting and receiving electronics and the battery power supply therefore may be contained in a case 36 worn on a belt surrounding the patient's abdomen. Information developed by the sensor 24 of the implant device 10 is telemetered to the external transducer 32 via RF transmission and is fed to the electronic module 36 for signal processing, storage and later analysis.

Figure 5:
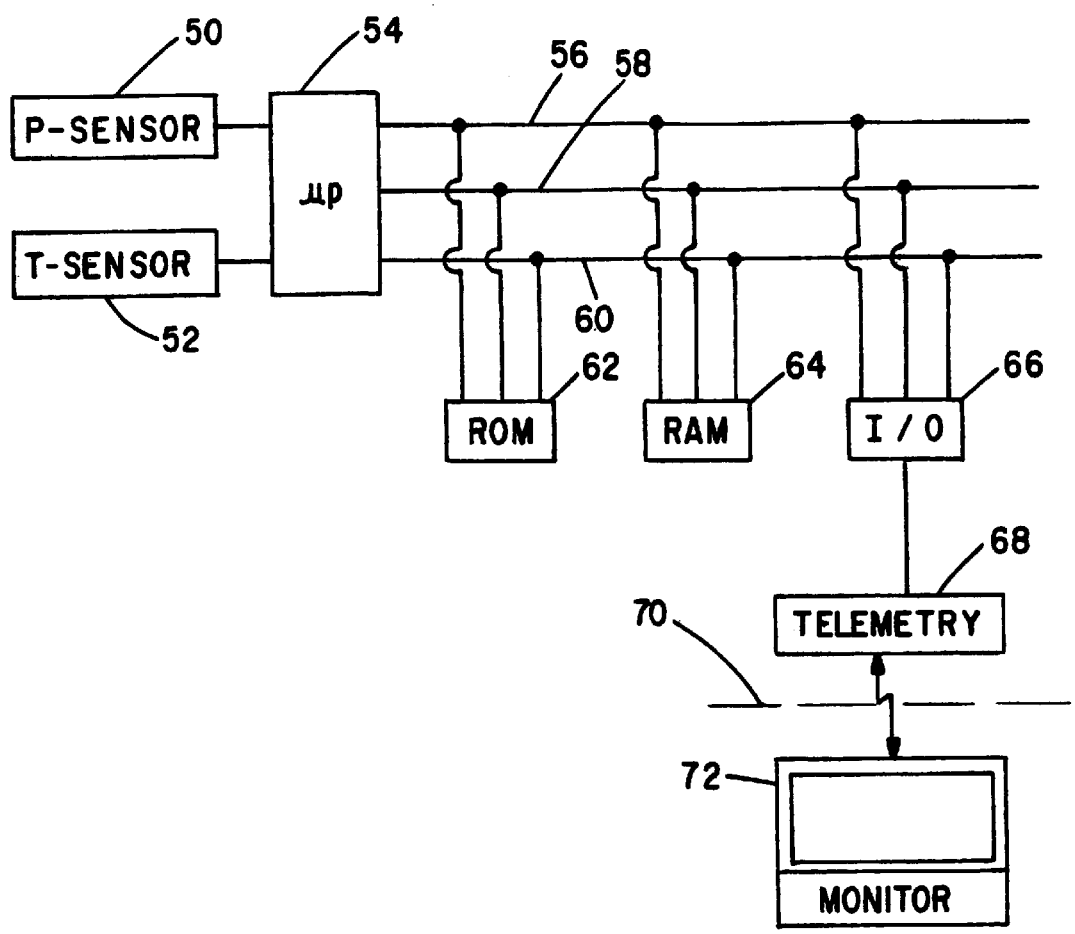
FIG. 5 is a block diagram of the integrated circuit chip forming a part of the implantable monitor apparatus.

FIG. 5 is a block diagram illustrating the circuitry contained within the housing 20 of the implant device. The output signals from the aforementioned pressure/temperature/flow transducers can readily be separated into two channels, one for carrying the pressure information and the other for carrying temperature information by appropriate filtering techniques, it being recognized that the output signal from the pressure sensor will be of a significantly greater frequency than that from the temperature sensor. Hence, in FIG. 5, both a pressure sensor 50 and a temperature sensor 52 are illustrated to indicate the dual channel nature, even though a single transducer device may be utilized. The analog output signal from both the pressure sensor 50 and the temperature sensor 52 are applied to an analog-to-digital converter forming a part of the on-board microprocessor 54. The microprocessor 54 includes an address bus 56, a data bus 58 and a control bus 60 to which are connected a ROM memory 62, a RAM memory 64 and an input/output interface 66. ROM 62 conventionally stores a program executable by the microprocessor 54 while RAM 64 may store programmable constants and intermediate data developed during the execution of the program. The I/O interface is attached to a telemetry circuit 68, allowing data carried on the data line 58 from the microprocessor and/or the RAM to be transmitted transcutaneously from the patient's body, represented by dashed-line 70 to an external monitor 72. The monitor 72 may be conveniently be a lap-top PC having the ability to receive and process the telemetry data from the implant and to deliver programming data to the implant device, via the telemetry link.

The temperature transducers illustrated in FIGS. 1 and 2 may comprise a thermistor, or thermocouple or an infrared sensor. A separate piezoelectric device can be utilized as a pressure sensor in a fashion indicated in the Brockway U.S. Pat. No. 4,846,191. It is also contemplated that a separate flow sensor may be made a component of the implantable monitor device or, alternatively, the temperature sensor may be used to assess flow using known thermodilution techniques.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A medical monitoring apparatus for use in a heart located in a body, the heart having first and second chambers separated by a septum, the apparatus comprising:
   a stent having a first end, a second end, and a lumen extending therebetween, the stent adapted for placement in the septum such that the first end contacts heart tissue adjacent the septum in the first chamber and the second end contacts heart tissue adjacent the septum in the second chamber, the stent further having a body extending between the first and second ends, either or both of the first and second ends having a cross sectional dimension larger than a cross sectional dimension of the body when the stent is placed in the septum;
   a sensor coupled to the stent for detecting a physiological parameter in the heart; and
   a telemetric transmitter coupled to the sensor and configured to transmit one or more signals representative of a detected physiological parameter percutaneously to a receiver.

2. The apparatus of claim 1, wherein the sensor is coupled to the stent in a manner such that, when the stent is placed in the septum, the sensor is exposed to blood in at least one of the first and second heart chambers.

3. The apparatus of claim 1, wherein the stent comprises one or more hooks on the first end and one or more hooks on the second end.

4. The apparatus of claim 1, wherein the detected physiological parameter is temperature, flow rate, or pressure.

5. The apparatus of claim 1, wherein the stent is self-expandable or balloon expandable.

6. The apparatus of claim 1, wherein the first and second heart chambers are left and right ventricles, and the septum is a ventricular septum.

7. The apparatus of claim 1, further comprising a power source coupled to the sensor and the telemetric transmitter.

8. The apparatus of claim 7, wherein the first and second heart chambers are left and right atria, and the septum is an atrial septum.

9. The apparatus of claim 1, wherein the first and second ends have diameters that are greater than a diameter of the lumen.

10. The apparatus of claim 1, wherein the stent exhibits a dumbbell configuration.

11. The apparatus of claim 10, wherein the stent self-expands into the dumbell configuration when released from the confines of a catheter.

12. A method for measuring one or more physiological parameters in a heart located in a body, the heart having first and second chambers separated by a septum, the method comprising:
   implanting a stent with an associated sensor within an opening formed through the septum between the first and second chambers;
   detecting a physiological parameter in the heart with the implanted sensor; and
   telemetrically transmitting one or more signals representative of the detected physiological parameter percutaneously to a receiver.

13. The method of claim 12, wherein the step of implanting the stent is performed by inserting the stent through a myocardium of either a left ventricle or a left atrium during open heart surgery.

14. The method of claim 12, wherein the step of implanting the stent is performed by delivering the stent via a catheter routed through a vascular system.

15. The method of claim 12, further comprising calibrating the sensor.

16. The method of claim 12, further comprising making an incision through the septum to form the opening.

17. The method of claim 12, wherein the stent comprises a first end, a second end, and a lumen extending therebetween, and the stent is implanted such that the first end is located in the first chamber, and the second end is located in the second chamber.

18. The method of claim 12, further comprising exposing the sensor to blood in at least one of the first and second chambers.

19. The method of claim 12, further comprising occluding the flow of blood through the stent.

20. The method of claim 12, wherein the detected physiological parameter is temperature, flow rate, or pressure.

21. The method of claim wherein step of implanting the stent comprises expanding the stent within the opening.

22. The method of claim 12, further comprising: implanting a power source within the body; and coupling power from the power source to the sensor.

23. A medical monitoring apparatus for use in a body, the apparatus comprising: a stent having a first end, a second end, and a lumen extending therebetween; a sensor coupled to the stent for detecting a physiological parameter in the body; an occluding member disposed within the lumen; and a telemetric transmitter coupled to the sensor and configured to transmit one or more signals representative of a detected physiological parameter percutaneously to a receiver.

24. The apparatus of claim 23, wherein the stent is self-expandable or balloon expandable.

25. The apparatus of claim 23, further comprising a power source coupled to the sensor and the telemetric transmitter.

26. A method for measuring one or more physiological parameters in a body, comprising:
   implanting a stent with an associated sensor within the body;
   occluding the flow of blood through the stent;
   detecting a physiological parameter in the body with the implanted sensor; and
   telemetrically transmitting one or more signals representative of the detected physiological parameter percutaneously to a receiver.

27. The method of claim 26, further comprising calibrating the sensor.

* * * * *